US010453211B1

(12) United States Patent
Christensen et al.

(10) Patent No.: US 10,453,211 B1
(45) Date of Patent: Oct. 22, 2019

(54) IMAGING HIDDEN OBJECTS

(71) Applicant: Southern Methodist University, Dallas, TX (US)

(72) Inventors: Marc P. Christensen, McKinney, TX (US); Prasanna Rangarajan, Dallas, TX (US)

(73) Assignee: Southern Methodist University, Dallas, TX (US)

( * ) Notice: Subject to any disclaimer, the term of this patent is extended or adjusted under 35 U.S.C. 154(b) by 135 days.

(21) Appl. No.: 15/659,528

(22) Filed: Jul. 25, 2017

(51) Int. Cl.
*G06T 7/62* (2017.01)
*G01N 21/01* (2006.01)
*G06T 1/00* (2006.01)
*G03H 1/04* (2006.01)

(52) U.S. Cl.
CPC .............. *G06T 7/62* (2017.01); *G01N 21/01* (2013.01); *G03H 1/04* (2013.01); *G06T 1/0007* (2013.01); *G06T 2207/10152* (2013.01)

(58) Field of Classification Search
CPC .............. G06T 7/62; G06T 1/0007; G06T 2207/10152; G06T 15/40; G03H 1/04; G01N 21/01
See application file for complete search history.

(56) References Cited

U.S. PATENT DOCUMENTS

| 8,565,499 | B2 * | 10/2013 | Zhao | G06T 11/003 382/128 |
| 8,665,361 | B1 | 3/2014 | Rangarajan et al. | |
| 9,131,223 | B1 | 9/2015 | Rangarajan et al. | |
| 10,107,747 | B2 * | 10/2018 | Baboulaz | G01N 21/55 |
| 2012/0069342 | A1 * | 3/2012 | Dalgleish | G01N 21/47 356/445 |

(Continued)

OTHER PUBLICATIONS

S. Tamano et al., "Phase-shifting digital holography with a low-coherence light source for reconstruction of a digital relief object hidden behind a light-scattering medium," Applied Optics, 2008, pp. 953-959, vol. 45, No. 5, Optical Society of America. (Year: 2008).*

(Continued)

*Primary Examiner* — Jennifer D. Carruth
(74) *Attorney, Agent, or Firm* — Fish & Richardson P.C.

(57) ABSTRACT

The present disclosure discloses an imaging system, method, and apparatus for identifying information of a hidden object. A light source generates a first beam of narrow-band light and a second beam of narrow-band light that has temporal fluctuations correlated with the first beam. The first beam is directed towards a first scattering surface and the second beam is directed towards a second scattering surface. The first scattering surface scatters the first beam to a scattered light that illuminates a hidden object, the hidden object reflects at least a portion of the scattered light towards the second scattering surface, the reflected light interferes with the second beam and produces an interference pattern on the second scattering surface. An image sensor detects irradiance of the interference pattern on the second scattering surface. An image processor calculates a complex-valued light field that represents information of the hidden object based on the detected irradiance of the interference pattern on the second scattering surface.

20 Claims, 13 Drawing Sheets

(56) References Cited

U.S. PATENT DOCUMENTS

| | | | |
|---|---|---|---|
| 2012/0242854 A1* | 9/2012 | Hoelscher | H04N 5/2628 |
| | | | 348/222.1 |
| 2013/0182224 A1* | 7/2013 | Schwiegerling | A61B 3/1015 |
| | | | 351/234 |
| 2018/0052088 A1* | 2/2018 | Sarkar | G01N 15/0227 |
| 2018/0096463 A1* | 4/2018 | Kim | G06T 5/002 |

OTHER PUBLICATIONS

Dairy Processing Handbook, Chapter 2, Bylund et. Al and put out by Tetra Pak, available at https://dairyprocessinghandbook.com/chapter/chemistry-milk (Year: 2019).*

Martin Laurenzis, Jonathan Klein, Frank Christnacher, "Transient light imaging laser radar with advanced sensing capabilities: reconstruction of arbitrary light in flight path and sensing around a corner ," Proc. SPIE 10191, Laser Radar Technology and Applications XXII, 1019103 (May 5, 2017) (Year: 2017).*

Martin Laurenzis, Frank Christnacher, Jonathan Klein, Matthias B. Hullin, Andreas Velten, "Study of single photon counting for non-line-of-sight vision," Proc. SPIE 9492, Advanced Photon Counting Techniques IX, 94920K (May 13, 2015) (Year: 2015).*

Jessica M. Schafer, Michael A. Marciniak, "The focusing of light scattered from diffuse reflectors using phase modulation", Proc. SPIE 8495, Reflection, Scattering, and Diffraction from Surfaces III, 84950O (Oct. 15, 2012) (Year: 2012).*

* cited by examiner

IMAGING HIDDEN OBJECTS

TECHNICAL FIELD

This disclosure relates to imaging and, more particularly, to identifying information of objects hidden from view.

BACKGROUND

Image sensing and acquisition technologies are often optimized for line-of-sight operations. Image sensing devices normally cannot discern objects that are beyond the line-of-sight or hidden from view. For example, a warfighter may not use an image sensing device to discern information of an armed assailants hidden behind a wall that obstructs the line-of-sight view.

Technologies for sensing hidden objects normally rely on a scattering surface, such as a wall to scatter light that can illuminate the hidden objects, and exploit light that returns from the hidden objects to recover information (such as geometric shape or image) of the hidden objects. Those technologies normally require some movements of the scattering surface to gain enough information diversity, which may not be practical in some situations.

SUMMARY

The present disclosure describes a system, apparatus, and method for identifying an image of an object hidden from view.

In some implementations, an imaging system for identifying information of a hidden object includes a light source that can emit narrow-band light. The light source may be a laser source, one or more light emitting diodes, or a broadband light source that emits light filtered by a narrow-band filter. In some cases, the narrow-band light may be coherent and have a linewidth of the narrow-band light is less than, or equal to, one nanometer. In some cases, the narrow-band light may have a frequency range in a visible portion of an electromagnetic spectrum, an infrared, an ultraviolet, or a millimeter wave spectrum. In some cases, the hidden object may be transmissive, translucent, opaque, or have a surface roughness greater than a wavelength of light.

In some implementations, the light source may generate an illumination beam of narrow-band light and a second beam of narrow-band light. The second beam may have temporal fluctuations correlated with the first beam. In some cases, a first beam splitter may be positioned along a propagation direction of the narrow-band light. In such cases, the first beam splitter can split the narrow band light into an illumination beam and a probe beam. In some cases, the illumination beam may be directed by the first beam splitter toward a first scattering surface that scatters the illumination beam and directs the scattered illumination beam toward a hidden object. Alternatively or additionally, the illumination beam may be directed or relayed by a phase modulator positioned along the propagation direction of the illumination beam toward the first scattering surface. In some cases, the phase modulator may also spatially modulate a phase of the illumination beam to create a phase shift of the illumination beam.

In some implementations, a phase modulator may be positioned along the propagation direction of the probe beam and direct the probe beam toward a light field of the scattered illumination beam reflected by the hidden object. The probe beam may interfere with the light field and create a first interference pattern on a second scattering surface. In some cases, the first scattering surface at least partially overlaps with the second scattering surface. In some cases, the first scattering surface and the second scattering surface may be surfaces of a wall, a door, a metallic structure, a frosted glass or a rough mirror.

In some implementations, an image sensor may be used to detect irradiance of the interference pattern on the second scattering surface, and an image processor may be used to calculates a complex-valued light field that represents information of the hidden object based on the detected irradiance of the interference pattern on the second scattering surface. The information of the hidden object may include a geometry, image, or hologram of the hidden object. Alternatively or additionally, the image processor may perform numerical approximation to calculate the information of the hidden object. The image processor may calculate the geometry of the hidden object based on a phase component of the complex-valued light field and the image of the hidden object based on a magnitude component of the complex-valued light field. Alternatively or additionally, the image processor may perform a field propagation, a Fourier transform, or a numerical approximation of the complex-valued light field. In some cases, the image sensor and the image processor may be included in the same camera.

In some implementations, the phase modulator may modulate the phase of the probe beam to introduce a first phase shift of the probe beam before the probe beam interferes with the light field of the scattered illumination beam diffracted by the hidden object. In some cases, the phase modulator may similarly modulate the phase of the probe beam to introduce a second phase shift of the probe beam and/or a third phase shift of the probe beam. Each phase shifted probe beam may create a different interference pattern with the light field of the scattered illumination beam diffracted by the hidden object. In some cases, the image sensor may detect the more than one interference pattern and the image processor may use the more than one interference pattern to calculate the complex-valued light field.

DESCRIPTION OF DRAWINGS

Like reference symbols in the various drawings indicate like elements.

DETAILED DESCRIPTION

The present disclosure describes techniques for recovering information, such as a hologram, an image, or any geometry of an object obstructed or hidden from an observer's view. In some implementations, the techniques can exploit the fact that real-world object surfaces are intrinsically rough at optical scale and consequently scatter light. The scattered light can traverse the scene and illuminate the object hidden from view. The scattered light acts as a virtual source of illumination for the object hidden from view. A fraction of the light striking the hidden object can be redirected towards a scattering surface, such as a wall, and subsequently, towards an image sensor used by an observer to sense the hidden object. The scattered light field intercepted by this surface may include obscured object information, so that the scattering surface may be viewed as a virtual detector. This suggests that light scattered by an optically rough surface that is visible to both the observer and the hidden object may be used to detect latent information of the hidden object.

In practice, the scattering surface may scramble the phase of the light from the hidden object. As a result, the image on the rough scattering surface, as observed by the image sensor, can be heavily corrupted by multiplicative noise arising from unknown scattering properties (such as complex reflectance) of the surface, and fails to yield discernible information on the hidden object. In some implementations, the disclosed techniques also include methods for circumventing the phase scrambling at the scattering surface to recover the hologram. The light used for recovering the hologram may be a narrow-band light, such as a laser. The light may be split into an illumination beam and a reference beam. At least one of the illumination beam or the reference beam may be spatially or temporally modulated to create diversity to the scattering properties of the surface. The diversity can be exploited to isolate the latent information of the hidden object from corrupting noise.

Figure 1:
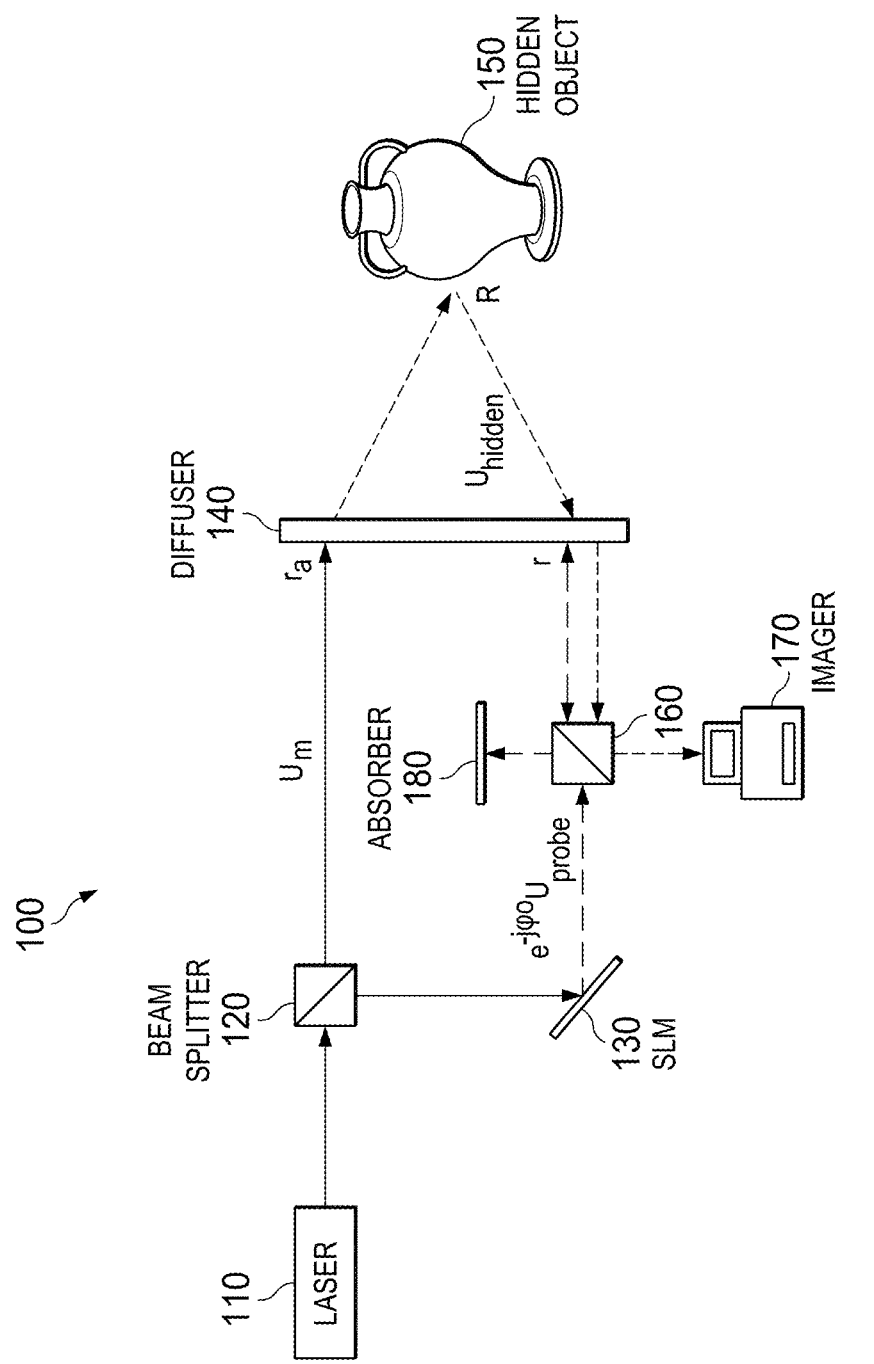
FIG. 1 illustrates an example imaging system for recovering a hologram of an object hidden from view.

FIG. 1 illustrates an example imaging system 100 for recovering a hologram of an object 150 hidden from view. At a high level, the example imaging system 100 includes a narrow-band light source 110, a first beam splitter 120, a spatial light modulator (SLM) 130, a second beam splitter 160, an absorber 180, and an imager 170. An object 150 is blocked from the view of the imaging system 100 by a diffuser 140. A diffuser 140 serves as the scattering surface that is simultaneously visible to the imager 170 and the object 150. An example of the diffuser 140 can be an opaque wall. The light scattered by the diffuser can illuminate the hidden object 150, and at least a portion of the scattered light may be diffracted towards the diffuser 140. As a result, the field of the diffracted light incident on the diffuser 140 may include information about the hidden object 150. The imager 170 that can observe the diffuser 140 may be able to detect the field.

In some implementations, the light source 110 can emit narrow-band light, such as a laser. A first beam splitter 120 positioned at the propagation direction of the emitted light can split the light into an illumination beam and a probe beam. The illumination beam and the probe beam can both illuminate on the diffuser 140. The probe beam can serve the purposes of: (1) converting the phase-variations in the diffracted field into intensity variations that can be sensed by a square law detector (not shown), and (2) heterodyning unresolved spatial frequencies in the diffracted field into a limited passband of an imager observing the diffuser. The diffuser 140 may scatter the illumination beam into a scattered light beam and direct the scattered light beam towards the hidden object 150. At least a portion of the scattered light beam may be diffracted by the hidden object 150. The diffracted light includes information of the hidden object 150 to be recovered by the imager 170.

In some implementations, the probe beam may be split by a second beam splitter 160 into a first split beam and a second split beam. The first split beam can be absorbed by an absorber 180. The second split beam can be directed to the diffuser 140 such that the incident field of the second split beam overlaps with the incident field of the light diffracted by the hidden object 150. This overlap can record an interference pattern or interferogram on the diffuser 140. In some cases, the probe beam may be directed by the first beam splitter 120 toward the diffuser 140 without being split by the second beam splitter 160 and overlaps with the light diffracted by the hidden object 150 to create the interferogram on the diffuser 140. In some cases, the probe beam may be spatially modulated by the SLM 130 to create a phase shift and/or directed by the SLM 130 to the diffuser. In such cases, the second beam splitter may be omitted.

The imager 170 may sense the intensity of the interferogram through scattered light from the diffuser 140 redirected by the second beam splitter 160. In some cases, the imager 170 may be positioned to directly sense the intensity of the interferogram without using the second beam splitter 160. Based on the intensity of the interferogram, the imager 170 may numerically resolve the complex-valued fields of the light, including the hologram through back propagation. In some implementations, the sensed intensity of the interferogram at the imager 170 can be expressed as:

$$i_{CCD}(x;\varphi_0) = \int_0^{t_{int}} dt \left| \int_{A_{CCD}} dr R_{diffuser}(r)(U(r, t - t_{cam}) + \right. \quad (1)$$

$$\left. e^{-i\varphi_0} U_{probe}(r, t - t_{cam} - \Delta t)) h_{cam}(x - r) \right|^2$$

$$= \int_0^{t_{int}} dt \left\{ \int \int_{A_{CCD}} dr dr' \left[ \begin{pmatrix} h_{cam}(x - r) \\ h_{cam}^*(x - r') \end{pmatrix} \times \right] \times \right. \quad (2)$$

$$\begin{pmatrix} R_{diffuser}(r) \\ R_{diffuser}^*(r') \end{pmatrix} \times \times$$

$$\left. \begin{pmatrix} [U(r, t - t_{cam}) + e^{-i\varphi_0} U_{probe}(r, t - t_{cam} - \Delta t)] \\ [U^*(r', t - t_{cam}) + e^{i\varphi_0} U_{probe}^*(r', t - t_{cam} - \Delta t)] \end{pmatrix} \times \right\}$$

The term $t_{int}$ represents the time interval over which the detector integrates photons. The term $t_{cam}$ represents the average time of flight of light paths from the diffuser to the detector. The term $\Delta t$ represents the difference in the travel time of the probe beam and the backscattered field incident on the diffuser. The terms r and x denote the transverse coordinates of points on the diffuser and detector, respectively. The term $\mathcal{R}_{diffuser}$ represents the multiplicative noise arising from the unknown scattering properties of the diffuser. The phase offset $\varphi_0$ represents the phase sift imparted to the probe beam.

In some implementations, the desired hologram $i_3(x; \Delta t)$ may be assembled by digitally recombining one or more interferogram images acquired using differently phased probe beams. The phase shifting of the probe beam may help in isolating the hologram term from the unwanted zeroth-order component and twin component. The expression for the hologram can be expressed as:

$$i_3(x; \Delta t) = \left[\frac{1}{4}i_{CCD}(x; 0, \Delta t) - \frac{1}{4}i_{CCD}(x; \pi, \Delta t)\right] + \quad (3)$$

$$\sqrt{-1}\left[\frac{1}{4}i_{CCD}\left(x; \frac{3\pi}{2}, \Delta t\right) - \frac{1}{4}i_{CCD}\left(x; \frac{\pi}{2}, \Delta t\right)\right]$$

$$= \int\int_{A_{CCD}} dr dr' \left[\begin{pmatrix} h_{cam}(x-r) \\ h^*_{cam}(x-r') \end{pmatrix} \times \begin{pmatrix} R_{diffuser}(r) \\ R^*_{diffuser}(r') \end{pmatrix} \times\right] \quad (4)$$

$$\left(\int_0^{t_{int}} dt \{U(r, t-t_{cam})U^*_{probe}(r', t-t_{cam}-\Delta t)\}\right)\right]$$

In some cases, the hologram may be heavily corrupted by multiplicative noises arising from unknown scattering properties (e.g., complex reflectance) of the diffuser 140. To combat this, a randomized wavefront error may be deliberately introduced to the imager 170. As a result, the optical point spread function (PSF) may exhibit stochastic character and may be largely uncorrelated with shifted copies of the PSF. This phenomenon can be expressed as:

$$(\int_{A_{CCD}} dx h_{cam}(x-r) h^*_{cam}(x-r') \propto \delta(r-r') \quad (5)$$

The use of stochastic optical blur may allow tailoring the second-order statistics of the multiplicative noise term $\mathcal{R}_{diffuser}$, and mitigating its influence by aggregating the field amplitude of the hologram $i_3(x; \Delta t)$. It follows from Equations (4)-(5) that $$\int_{A_{CCD}} dx[i_3(x; \Delta t)] = \quad (6)$$

$$\int_{A_{CCD}} dr |R_{diffuser}(r)|^2 \times [U^*_{probe}(r, t-t_{cam}-\Delta t)U(r, t-t_{cam})]$$

In some cases, the transmissivity of the diffuser 140, denoted as $|\mathcal{R}_{diffuser}(r)|^2$, may remain unchanged over the spatial extent of the probe beam. The expression for the integrated field amplitude may then be reduced to an exact linear projection expressed as $\langle \mathcal{U} | \mathcal{U}^*_{probe} \rangle$. In such cases, a hologram may be assembled from the projections $\langle \mathcal{U} | \mathcal{U}^*_{probe} \rangle$, by selecting probe beams from an orthonormal basis set. Examples of basis sets may include spatially uniform fields (planar/spherical) and stochastic fields. The assembly process can mirror the reconstruction scheme in a single pixel compressed sensing imager, so that the machinery of compressive sensing can be exploited to assemble the hologram. In some implementations, a lattice of light spots may be used to sample the diffracted field at the diffuser 140, at resolutions commensurate with the transverse extent of a single light spot.

Figure 2A:
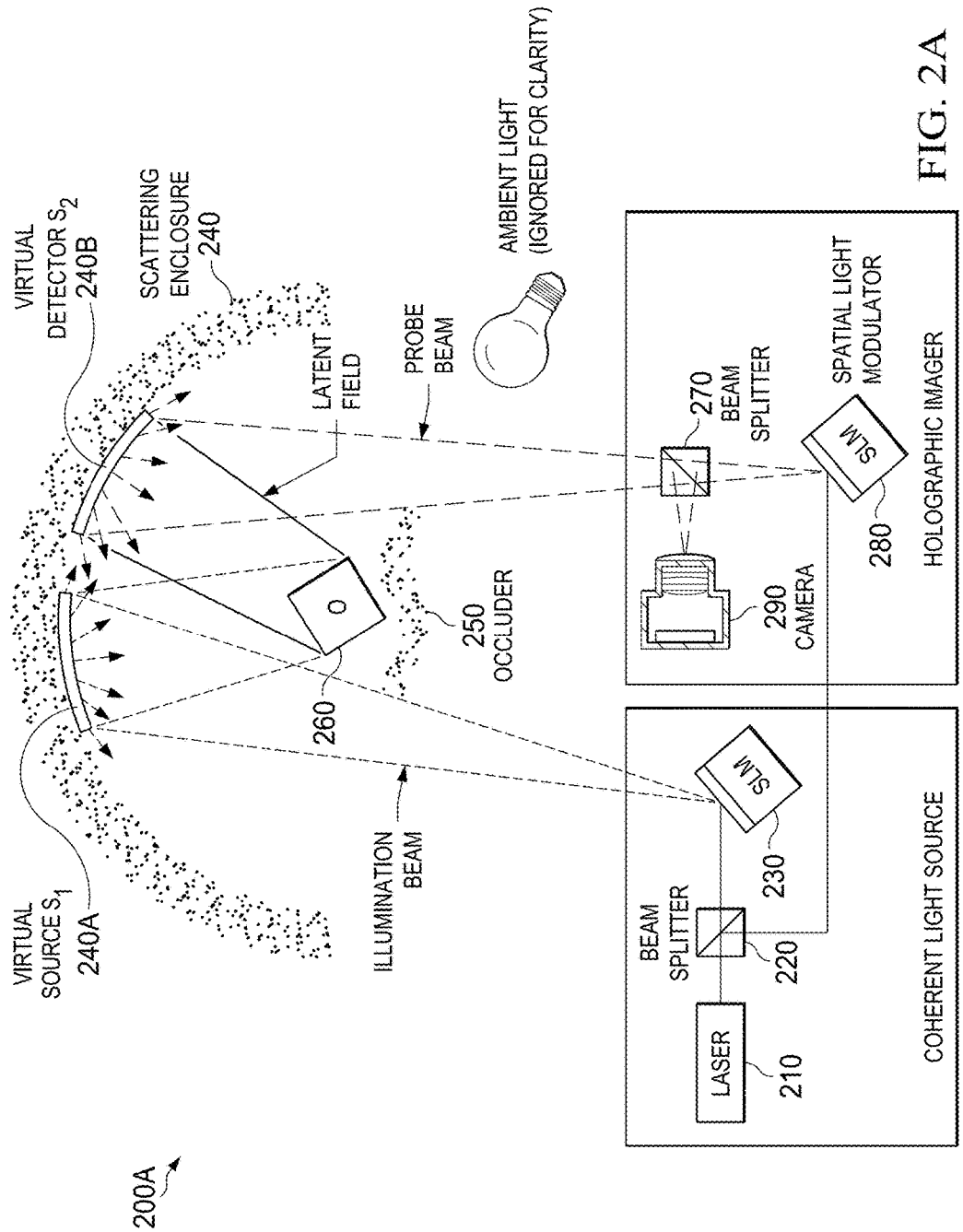
FIG. 2A illustrates another example imaging system for recovering an image of an object hidden from view.

FIG. 2A illustrates another example imaging system 200A for recovering an image of an object 260 hidden from view. The example imaging system 200A includes a laser source 210, a first beam splitter 220, a first SLM 230, a second beam splitter 270, a second SLM 280, and a camera 290. An object 260 is obstructed from view of the camera 290 by an occluder 250. A scattering enclosure 240 is simultaneously visible to the camera 290 and the object 260.

The laser source 210 can generate coherent, narrow-band laser light. Coherent light can be a beam of photons that have substantially the same frequency and are all at substantially the same frequency. The first beam splitter 220 may be positioned at the propagation direction of the light source to split the laser light to an illumination beam and a probe beam. The illumination beam may traverse to the scattering enclosure 240 and is scattered by the enclosure 240 to illuminate the hidden object 260. The portion of the scattering enclosure 240 surface (surface $S_1$) that scatters the illumination beam can be considered as a virtual source 240A of light. At least a portion of the light scattered by the virtual source 240A may be diffracted by the hidden object 260 and traverses back to illuminate another portion of the scattering enclosure (surface $S_2$) 240B. Since the light incident on surface $S_2$ is diffracted by the hidden object 260, it includes hologram information about the hidden object 260. Therefore, surface $S_2$ may serve as a virtual detector 240B that records information about the hologram of the hidden object 260. The camera 290 may image the virtual detector 240B surface and use the captured data to recover the hologram. In some implementations, the imaging optics within the camera module 290 may serve the purpose of relaying the light distribution at the virtual detector 240B onto a remote physical detector (not shown) for image recovery. In some implementations, a first and/or a second SLMs 230, 280 may be used to spatially and/or temporally modulate the light beams to tailor the light distribution at the virtual source 240A and/or the virtual detector 240B. In some cases, the first SLM 230 may be positioned at the propagation direction of the illumination beam to relay or direct the illumination beam towards the scattering enclosure surface $S_1$ or the virtual source 240A. In some implementations, the second SLM 280 may be positioned at the propagation direction of the probe beam to relay or direct the probe beam towards the scattering enclosure surface $S_2$ 240B. In some cases, a second beam splitter 270 may be used to relay or direct the probe beam towards the scattering enclosure surface $S_2$ 240B and/or relay or direct the light distributed on the scattering enclosure surface $S_2$ 240B to the camera 290. The camera 290 may include an image sensor (not shown) to detect or sense light, and an image processor (not shown) to perform digital image processing.

As aforementioned, the light scattered by the virtual source 240A can illuminate the hidden object 260, and a portion of the light is directed towards the virtual detector 240B. A hologram can be identified by detecting the light field incident on the virtual detector 240B. In some implementations, the process of detecting and recovering a hologram can be performed through numerical computations. The light field may be represented by complex-valued variables. The hologram may then be calculated by resolving the complex values of the latent field.

In some cases, the example imaging system 200A can use coherent detection to determine the complex-valued field. Since the illumination beam and the probe beam are originated from the same laser source 210, their temporal fluctuations are highly correlated. Therefore, the probe beam can be used to mix with the latent field created by light diffracted from the illumination beam for coherent detection. The mixture of the probe beam and illumination beam can create the interferogram on the virtual detector 240B. The camera 290 may capture the interferogram information and use it to numerically compute the latent scene information of the hidden object 260.

Figure 2B:
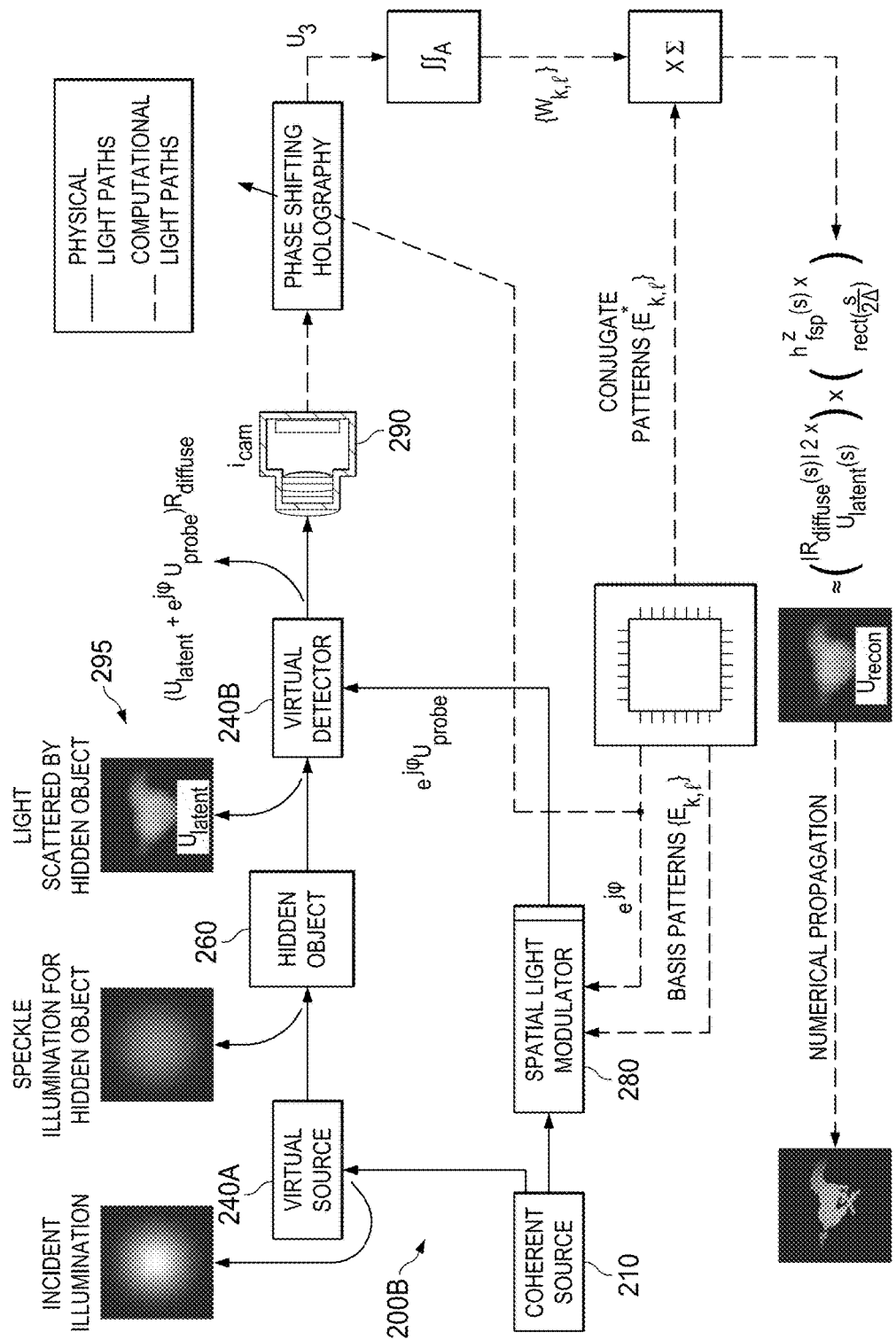
FIG. 2B illustrates an example workflow of computing an image information of the object hidden from view.

FIG. 2B illustrates an example workflow 200B for computing the image information of the object 260 hidden from view. For the purpose of illustration, it is assumed that the example workflow is based on the example imaging system 200A illustrated in FIG. 2A. It is to be understood that the example workflow can be used for computing latent scene information for other implementations. One or more elements of the imaging system 200A are intentionally hidden from the workflow 200B diagram for simplicity of illustration.

As discussed in the illustration of FIG. 2A, the camera 290 may include an image sensor for detecting the interferogram recorded at the virtual detector 240B. The image sensor may then convey the detected information to an image processor to perform digital image processing. In some cases, the image processing may be delegated to be performed by a remote detector separate from the camera 290. In some implementations, assume that the camera 290 has a space-invariant blur $h_{cam}$, a magnification factor m, and an active sensor area $\mathcal{A}$ meter². The expression for the captured image intensity from the interferogram can be expressed as:

$$i_{cam}(x; \varphi_0) = \qquad (7)$$

$$\int_0^{t_{int}} dt \left| \int_{\mathcal{A}} dr \left\{ R_{diffuse}(r) \binom{U_{latent}(r, t - t_{cam}) +}{e^{-i\varphi_0} U_{probe}(r, t - t_{cam})} \right\} h_{cam}(x - r) \right|^2$$

where $r = mv_d$

The terms $t_{int}$, $t_{cam}$ represent the integration time and average time of flight of light paths from the virtual detector 240B to the physical detector of the camera 290. The terms $r=mv_d$ and x denote the transverse coordinates of points on the virtual detector 240B and physical detector of the camera 290, respectively. The term $\mathcal{R}_{diffuse}$ represents the complex-valued reflectance associated with the virtual detector surface 240B.

Expanding equation (7) can yield a mixture of three components that represent the captured camera image of the interferogram: (1) A zeroth-order component expressed as $|\mathcal{R}_{diffuse} \mathcal{U} \otimes h_{cam}|^2 + |\mathcal{R}_{diffuse} \mathcal{U}_{probe} \otimes h_{cam}|^2$, (2) a twin component expressed as $\text{conj}(\mathcal{R}_{diffuse} \mathcal{U} \otimes h_{cam}) \times (\mathcal{R}_{diffuse} \mathcal{U}_{probe} \otimes h_{cam})$, and (3) a hologram component of interest expressed as $(\mathcal{R}_{diffuse} \mathcal{U} \otimes h_{cam}) \times \text{conj}(\mathcal{R}_{diffuse} \mathcal{U}_{probe} \otimes h_{cam})$. The task then becomes isolating the hologram component from the zeroth-order component and the twin component.

As shown in equation (7), a phase shift $\varphi_0$ can be introduced to the probe beam field represented by $\mathcal{U}_{probe}$. This phase shifting may be enabled by modulating the probe beam using the second SLM 280. In some implementations, a phase shift may also be introduced by modulating the illumination beam using the first SLM 230. The phase shift may help isolate the hologram field denoted by $\mathcal{U}_3$ from the interfering zeroth-order component and twin components. The hologram field $\mathcal{U}_3$ may be expressed as:

$$U_3(x) = \int \int_{\mathcal{A}} drdr' \left[ \binom{h_{cam}(x-r) \times}{h^*_{cam}(x-r')} \right] \times \binom{R_{diffuse}(r) \times}{R^*_{diffuse}(r')} \times \qquad (8)$$

$$\left( \int_0^{t_{int}} dt U(r, t-t_{cam}) U^*_{probe}(r', t-t_{cam}) \right)$$

$$= \left\{ \int \int_{\mathcal{A}} drdr' \left[ \binom{h_{cam}(x-r) \times}{h^*_{cam}(x-r')} \times \binom{R_{diffuse}(r) U(r) \times}{R^*_{diffuse}(r') U^*_{probe}(r')} \right] \right\} \times$$

$$\left\{ \int_0^{t_{int}} \binom{\exp(-i2\pi\bar{v}(t-t_{cam})) \times}{\exp(i2\pi\bar{v}(t-t_{cam}))} dt \right\}$$

$$= (R_{diffuse} U_{latent} \otimes h_{cam}) \times \text{conj}(R_{diffuse} U_{probe} \otimes h_{cam})$$

The integrated amplitude of the complex-valued hologram $\mathcal{U}_3(x)$ can be computed as:

$$\int_A U_3(x)dx = t_{int} \times \left\{ \int \int_A drdr' \left[ \left( \int_A dx h_{cam}(x-r) h^*_{cam}(x-r') \right) \times \qquad (9) \right. \right.$$

$$\left. \left. \binom{R_{diffuse}(r) U(r) \times}{R^*_{diffuse}(r') U^*_{probe}(r')} \right] \right\}$$

$$= t_{int} \times \left\{ \int \int_A drdr' \left[ \chi_{cam}(r'-r) \binom{R_{diffuse}(r) U(r) \times}{R^*_{diffuse}(r') U^*_{probe}(r')} \right] \right\}$$

where $\chi_{cam}(r'-r)$ $$= \left( \frac{\rho_{max}}{r'-r} \right) \times J_1 \left( 2\pi \frac{r'-r}{\rho_{max}} \right)$$

The term $\rho_{max}$ in equation (9) can represent the cutoff frequency of the imaging optics for circular pupils. If the camera blur is compactly supported, i.e., $(\chi_{cam}(r'-r) \approx \delta(r'-r))$, the expression for integrated amplitude of the hologram may be approximated as:

$$w \stackrel{def}{=} \left( \int_A U_3(x)dx \right) \approx t_{int} \times \left\{ \int_A dr |R_{diffuse}(r)|^2 U(r) U^*_{probe}(r) \right\} \qquad (10)$$

It can be shown from equation (10) that the integrated amplitude (w) is invariant to phase distortions arising from surface roughness at the virtual detector 240B. Furthermore, $w \propto \langle \mathcal{U} | \mathcal{U}_{probe} \rangle$ for virtual detector surface 240B with constant reflectivity. As such, the hologram image field $\mathcal{U}_{recon}$ may be assembled from inner product measurements associated with an orthonormal basis set. Assume that the probe beam field $\mathcal{U}_{probe}$ is obtained by paraxial propagation of a spatial pattern ($E_{k,l}$) defined on the P×P grid of the SLM 280 with pixel pitch $\Delta$ µm. This implies that $\mathcal{U}_{probe} = E_{k,l} \otimes h_{fsp}^z$, where $h_{fsp}^z$ is the free-space blur associated with a z meter path from the SLM 280 to the virtual detector 240B. Let $w_{k,l}$ denote the integrated amplitude associated with the spatial pattern $E_{k,l}$, the hologram of the hidden scene elements may be assembled from the $P^2$ inner product measurements associated with the $P^2$ basis patterns, as shown in equation (11), which in turn can be calculated to yield the expression in equation (12).

$$U_{recon}(s) \stackrel{def}{=} \sum_{k,l=1}^{P} w_{k,l} E^*_{k,l}(s) \qquad (11)$$

$$\approx \left( \int_A dr |R_{diffuse}(r)|^2 U(r) \left\{ \int_{A_{slm}} ds' h_{fsp}^z(s'-r) \text{rect}\left( \frac{s-s'}{2\Delta} \right) \right\} \right) \qquad (12)$$

$$\approx \kappa (|R_{diffuser}(s)|^2 U(s)) \otimes h_{fsp}^z(s) \otimes \text{rect}\left( \frac{s}{2\Delta} \right)$$

The rect( . . . ) function in equations (11) and (12) emerges from the orthogonality of the basis patterns. As expressed in equation (12), the image of the hidden object 260 may be recovered by numerical back-propagation of the complex-valued image field $\mathcal{U}_{recon}$.

In some implementations, the speckle-like appearance of the secondary illumination 295 may arise from scattering at the virtual source 240A. This scattering may not impact image recovery, but it may introduce speckle artifacts in the reconstruction. In some cases, the complex-valued reflectivity of the scattering surface $\mathcal{R}_{diffuse}$ as experienced by the field and the probe beam may be identical, as the speckle fields produced by the plane wave components constituting the illumination beam and the probe beam can exhibit a large degree of spatial correlation in accord with the "memory effect." The "memory effect" (in reflection mode) may stem from near identical optical path length differences experienced by two mutually coherent beams with small angular separation.

Figure 3A:
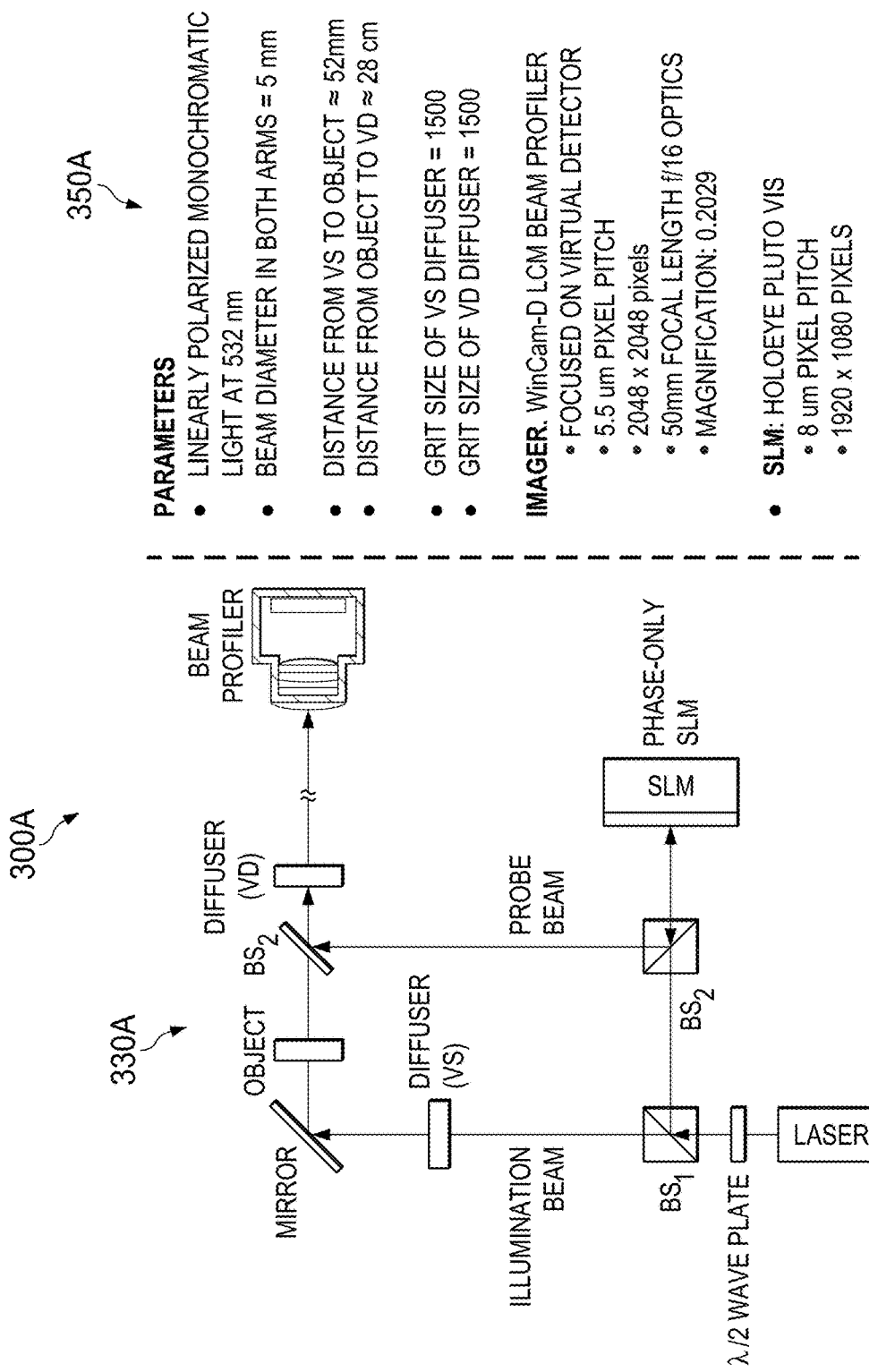
FIG. 3A illustrates an example experimental imaging system for recovering an image of an object hidden from view.

FIG. 3A illustrates an example experimental imaging system 300A for recovering an image of an object hidden from view. In this example system 300A, object 330A to be detected is embedded between two diffusers. The technologies used by the example imaging system 300A to recover the image may include interferometry, holography and super-resolution.

As discussed previously, the example imaging systems disclosed in the present disclosure can recover images by sensing the interferogram created by the light scattered by the obscured objects and the probe beam, as viewed on a remote scattering surface. Therefore, an interferometer may be used in the experiment of the example imaging system 300A. In the present example, a free-space Mach-Zehnder interferometer may be used. An example specification 350A of the interferometer is shown on the right hand side of FIG. 3A.

Figure 3B:
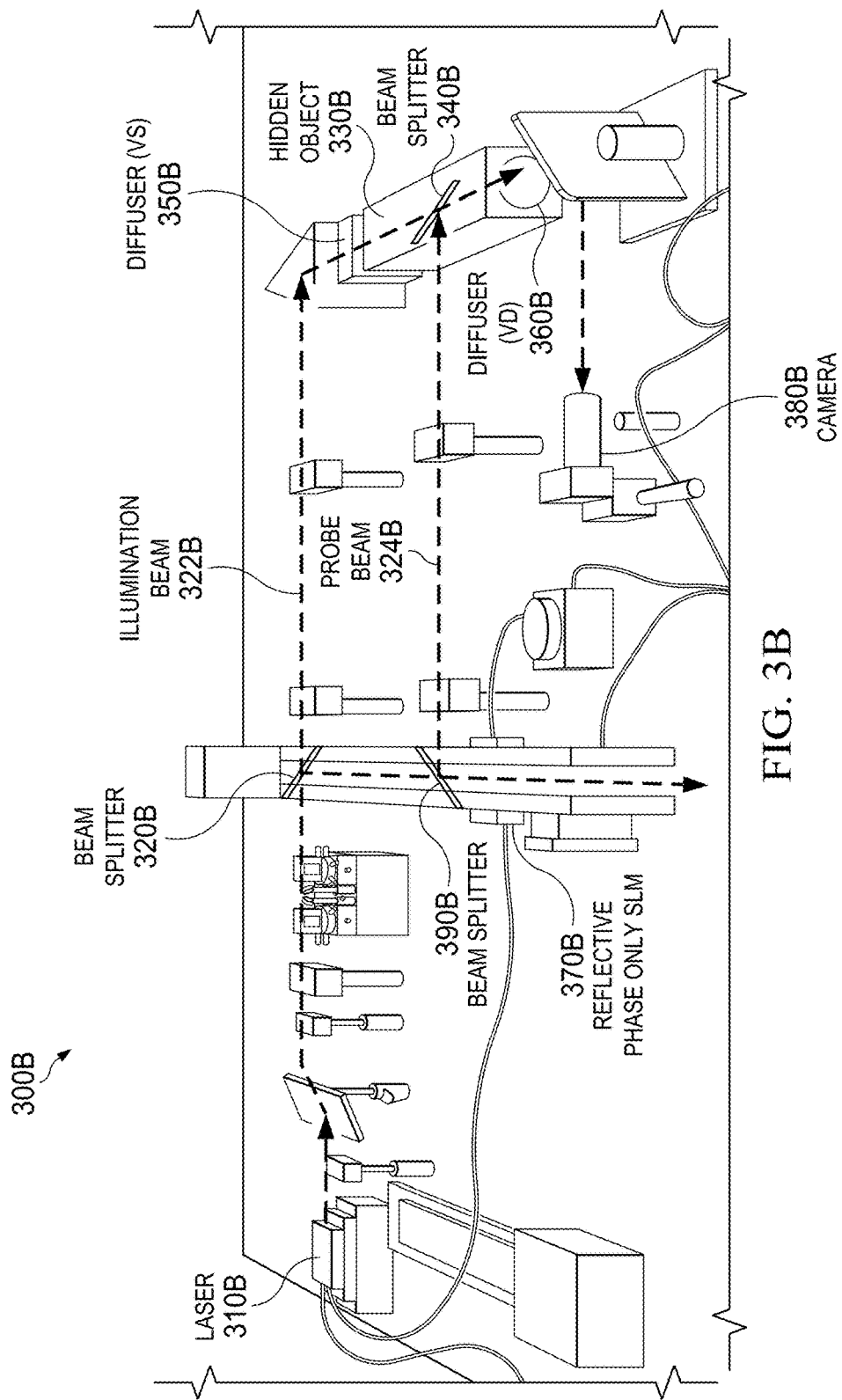
FIG. 3B shows example apparatuses of the example experimental imaging system.

FIG. 3B shows example apparatuses 300B of the example experimental imaging system 300A. The example apparatuses 300B include a non-polarizing cube beam splitter 320B, endowed with a laser notch filter thin film coating at 532 nm. The beam splitter 320B can be used to derive an illumination/object beam 322B and a probe/reference beam 324B from a single collimated laser source 310B. The propagation length of each arm of the interferometer may exceed two meters to mimic the observation of a hidden object at standoff. The hidden object 330B can be a transmissive element that is embedded between two ground glass diffusers 350B and 360B. The diffusers may serve as surrogates for the scattering wall. Light emerging from diffuser 350B may act as virtual source. Diffuser 360B may intercept light scattered by a hidden object 330B, thereby acting as a virtual detector.

A pellicle beam splitter 340B may be used to combine the scattered light from the hidden object with the probe beam and direct the light towards the camera using a folding mirror. The use of a pellicle beam splitter 340B can avoid path length distortions in the plane wave components that make up the latent field. The angular separation of the scattered field and the probe beam can be controlled by adjusting the orientation of the pellicle beam splitter 340B.

A diffraction limited imager or camera 380B may be used to record the interference patterns observed at the virtual detector surface. The reflective SLM 370B in the reference arm may provide the phase diversity required to isolate the hologram term from the zeroth order and twin components. The use of a SLM 370B may allow engineering probe beams from an orthonormal basis, while introducing precise phase-retardation/path length differences between the interferometer arms. Liquid Crystal on Silicon (LCoS) devices SLM such as the Holoeye PLUTO may afford such capabilities at real-time rates. In some cases, the Parallel-Aligned (PA-LCoS) variety is of special interest in that it permits phase-only modulation of the incident light without residual amplitude modulation. A half-wave plate beam splitter 390B in the laser beam path may be used to help in aligning the polarization state of the laser beam with the slow axis of the phase-only SLM 370B. This can avoid undesired coupling between the fast and slow (phase-shifted) components of the light emerging from the SLM 370B.

Figure 3C:
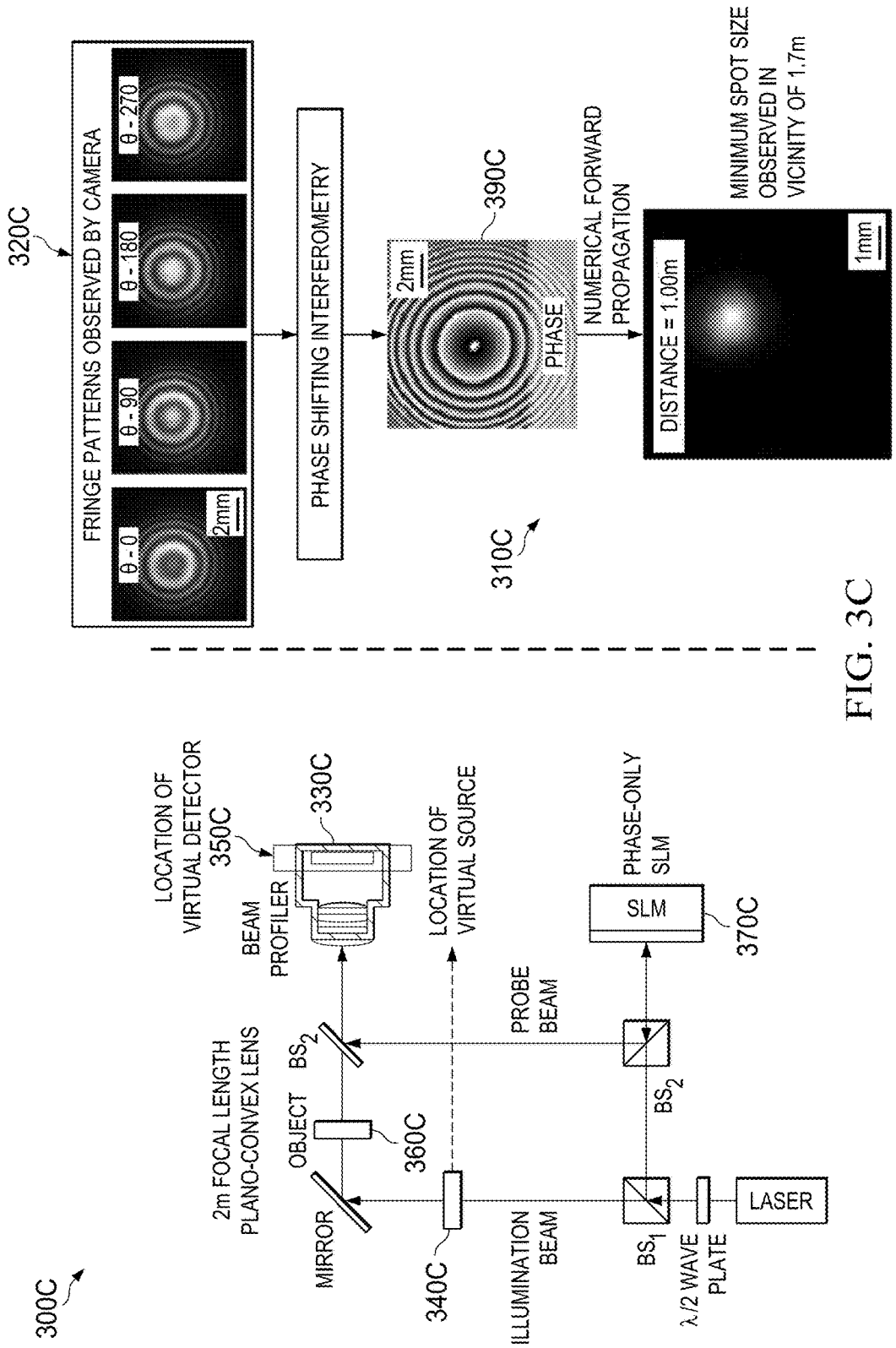
FIG. 3C illustrates an example experiment for recovering an image and the corresponding experiment result.
Figure 3D:
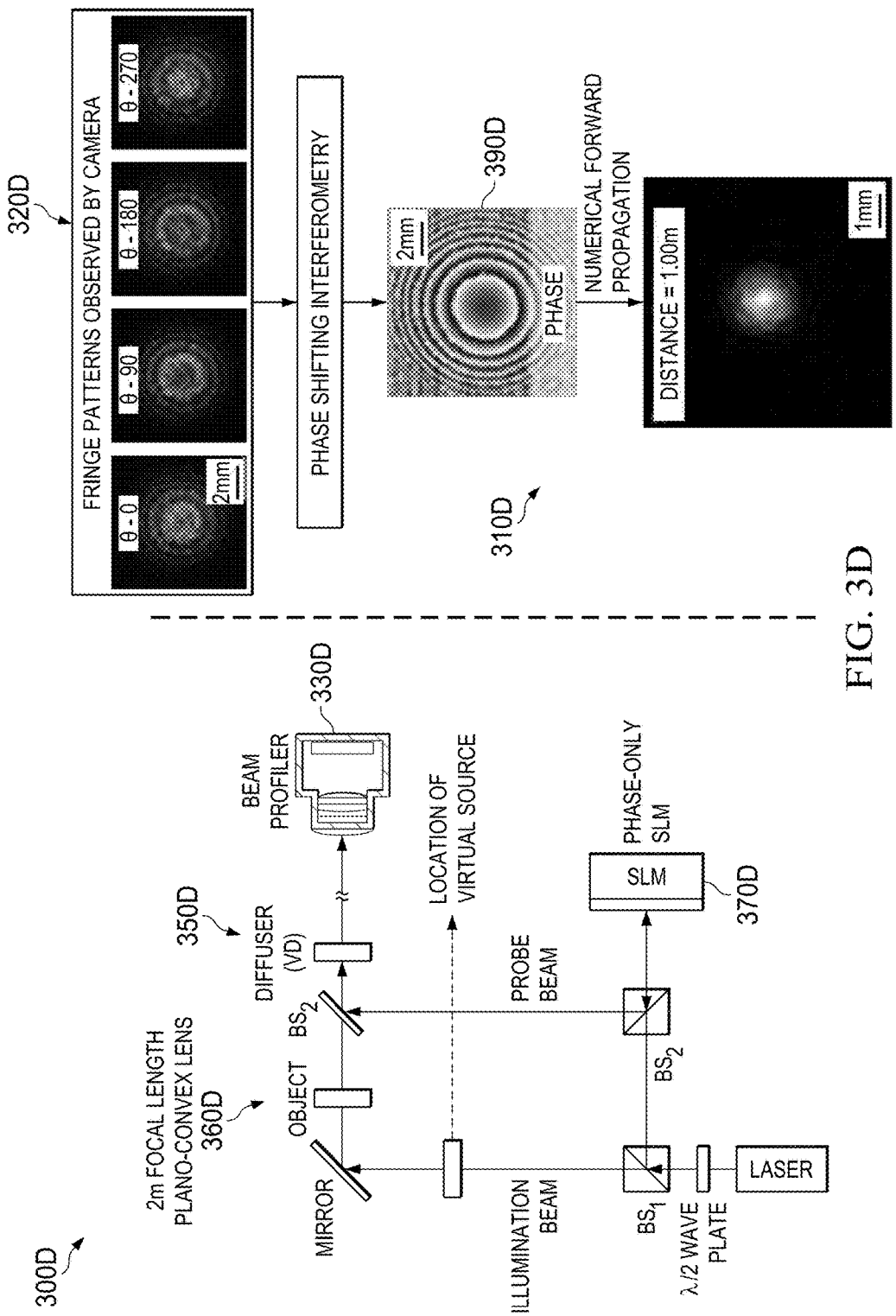
FIG. 3D illustrates another example experiment for recovering an image and the corresponding experiment result.
Figure 3E:
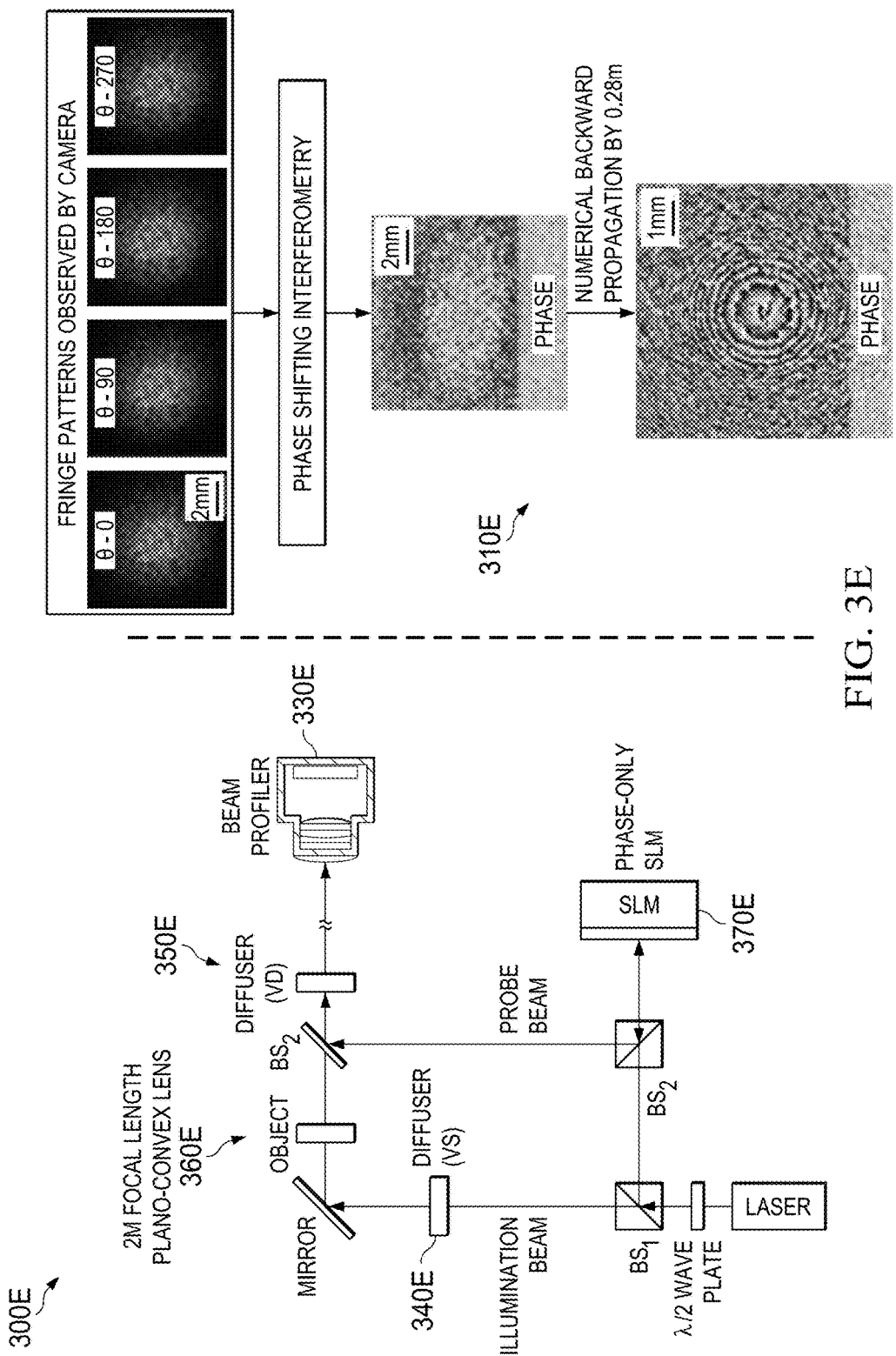
FIG. 3E illustrates yet another example experiment for recovering an image and the corresponding experiment result.

A series of increasingly sophisticated experiments using experimental system 300A and apparatuses 300B are illustrated in FIGS. 3C-3E to show the feasibility of image recovery techniques described in the present disclosure. The development of the experiments may generally include two phases. The first phase may demonstrate the feasibility of image recovery, identify design requirements, and explore practical limits. The second phase may examine approaches to circumvent those limits.

FIG. 3C illustrates an example experiment 300C for recovering an image and the corresponding experiment result 310C. In the illustrated experiment 300C, the goal is to acquire a "gold-standard" hologram of the hidden object 360C. The camera 330C is repositioned to enable the acquisition of the hologram, as sensed at the virtual detector 350C. The hologram is associated with a two-meter focal length planoconvex lens embedded between the two diffusers that also serve as virtual source 340C and virtual detector 350C.

The "gold-standard" hologram 310C may be recovered by processing four images of the fringe patterns 320C obtained by stepping through four phase shifts on the reflective SLM 370C. The radial structure of the fringes is consistent with the interference of a collimated probe beam with the converging beam emerging from the hidden lens. The phase of the estimated hologram is shown in the phase inset 390C. Numerical propagation of the estimated hologram shows the converging/focusing structure of the phasefront emerging from the plano-convex lens. Furthermore, it is observed that the minimum spot size can be obtained for a propagation distance of 1.7 meters, consistent with the separation between the phase object 340C and the camera 330C. The experiment result of the "gold-standard" hologram 310C may have reaffirmed the notion that scattering at the virtual detector corrupts the phase of the hidden object field, while still preserving hidden object information.

FIG. 3D illustrates another example experiment 300D for recovering an image and the corresponding experiment result 310D. The illustrated example experiment 300D may be considered a natural progression of example experiment 300C illustrated in FIG. 3C. In this example experiment 300D, diffraction limited imaging optics may be used to relay the fringe pattern observed at the virtual detector 350D to a remote image detector 330D.

The hologram of the phase object can be recovered by processing four images 320D of the fringe patterns obtained by stepping through four phase shifts on the reflective SLM 370D. The radial structure of the fringes is consistent with the interference of a collimated probe beam with the converging beam emerging from the hidden lens. The distinct speckle structure in the fringe patterns arise from scattering at the virtual detector 350D surface. The phase of the estimated hologram is shown in the phase inset 390D. Numerical propagation of the estimated hologram shows the converging/focusing structure of the phasefront emerging from the plano-convex lens. Furthermore, it is observed that the minimum spot size is obtained for a propagation distance of 1.7 meters, consistent with the separation between the phase object 340D and the detector 330D. The experiment result 310D reaffirms the notion that scattering at the virtual detector corrupts the phase of the hidden object field, while still preserving object information.

FIG. 3E illustrates yet another example experiment 300E for recovering an image and the corresponding experiment result 310E. The example experiment 300E can be used to examine the impact of scattering at the virtual source 340E and virtual detector 350E. Similar to example experiment 300D, diffraction limited optics may be used to relay the fringe pattern observed at the virtual detector 350E to the remote detector 330E. The sections of the apparatus leading up to the virtual detector 350E resemble the experimental setup of example experiment 300D. The distinction may lie in computational recording of the hologram on a scattering surface, and relaying of the hologram to the remote detector 330E.

Examination of the phase of the hologram confirms the lack of any discernible structure. Numerical back propagation of the hologram by a distance commensurate with the spacing between the virtual detector 350E and the hidden phase object (0.28m) 360E reveals a distinctly quadratic phase structure. The experiment result 310E shows that scattering at the virtual source 340E and virtual detector 350E may corrupt the phase of the hidden object field, while still preserving object information.

Figure 4:
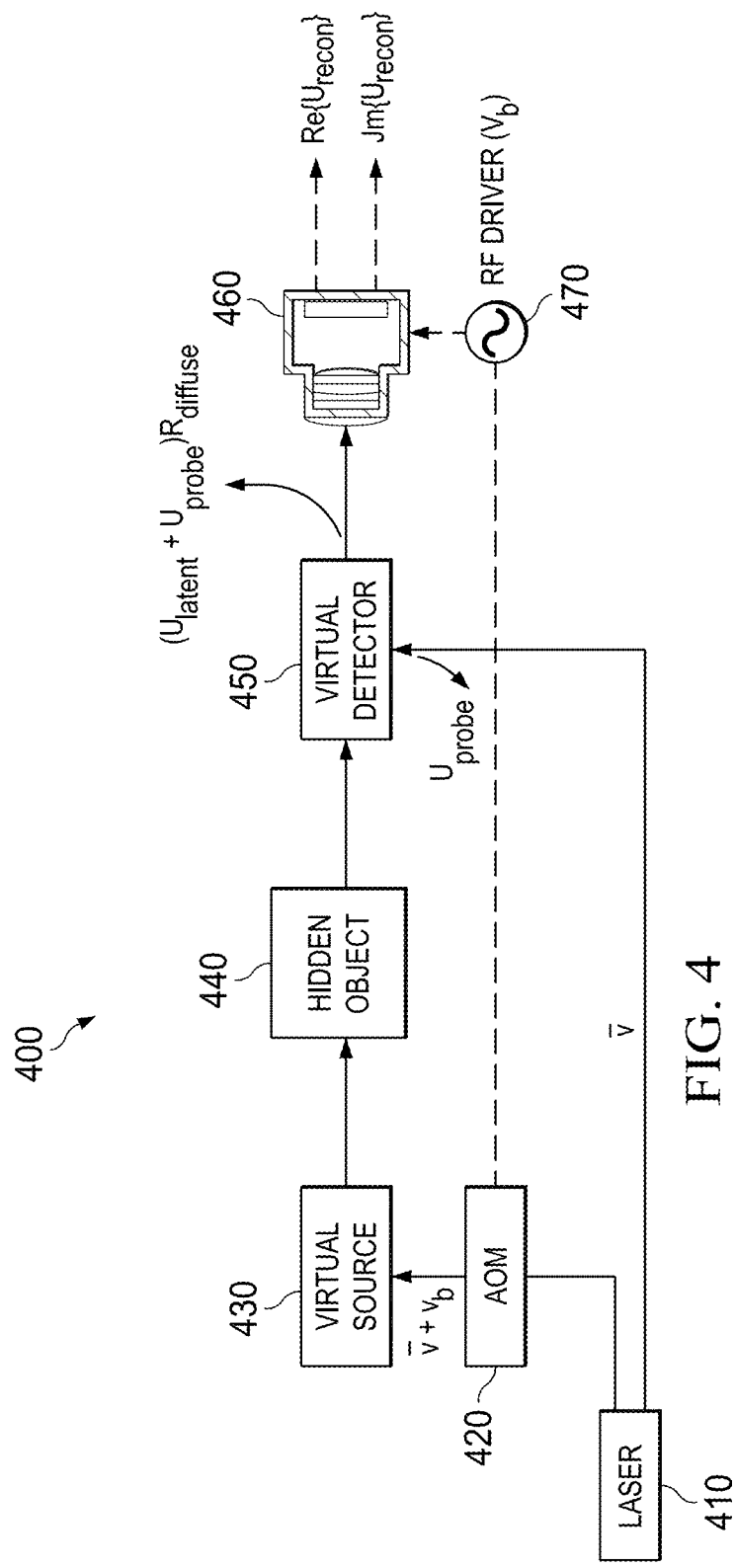
FIG. 4 illustrates an example single-shot imaging system for recovering an image of an object hidden from view.

FIG. 4 illustrates an example single-shot imaging system 400 for recovering an image of an object 440 hidden from view. The aforementioned implementations generally exploit spatial diversity in the phase of the split beams to perform image recovery. The hologram component is isolated from the corrupting influence of the zeroth-order component and twin component based on knowledge of the phase shift applied to the illumination beam and/or probe beam. The hologram image is assembled by processing a sequence of interference pattern images acquired under the phase shifts of the probe beam. By contrast, the example imaging system 400 illustrated in FIG. 4 can adopt a single-shot approach to recover the hologram term instead of assembling and processing a sequence of images. The approach is based on an operation of a heterodyne interferometer, which can exploit diversity in the temporal frequency instead of spatial diversity in the phases of the beams.

At a high level, the example single-shot imaging system includes a laser source 410, an Acousto-optic modulator (AOM) 420, a virtual source 430 surface, a virtual detector 450 surface, a lock-in camera 460, and a RF driver 470. The example single-shot imaging system 400 can use the virtual source 430 as scattering surface for diffuse illumination and perform indirect imaging of the hidden objects 440 through the virtual detector 450 surface. The single-shot imaging system 400 can use one or more AOM 420 to upshift the frequency of the illumination beam by $v_b$. In some implementations, the frequency shift $v_b$ may be generated by an RF driver 470. The difference $v_b$ in the temporal frequencies of the interfering fields may be much less than the frequency of the laser light, $\bar{v}$, so that the wavelength of the light in the two beams is nearly identical. It is to be understood that the AOM 420 may apply different temporal frequency shifts for different implementations.

The computation of image of the hidden object 440 using the example single-shot imaging system can begin from using the lock-in camera 460 to capture the instantaneous light intensity of the interferogram distributed on the virtual detector 450. The light intensity sensed by the lock-in camera 460 can be expressed as:

$$i_{cam}(x, t) = \left| \int_A dr \left\{ R_{diffuse}(r) \left( \begin{array}{c} U(r, t) + \\ U_{probe}(r, t) \end{array} \right) \right\} h_{cam}(x - r) \right|^2 \quad (13)$$

where $r = mv_d$

The terms $r = mv_d$ and x denote the transverse coordinates of points on the virtual detector 450 and the lock-in camera 460, respectively. The term $\mathcal{R}_{diffuse}$ represents the complex-valued reflectance associated with the virtual detector 450 surface.

In some implementations, it is assumed that the laser source 410 is monochromatic. As such, the expressions for the instantaneous field in illumination beam and probe beam of the interferometer may be expressed in the complex phasor form as:

$$\mathcal{U}(r,t) = A(r)\exp(-i(\bar{v}+v_b)t)$$

$$\mathcal{U}_{probe}(r,t) = A_{probe}(x)\exp(-i\bar{v}t) \quad (14)$$

Incorporating equation (14) into equation (13) can yield the following revised expression for the instantaneous detector intensity:

$$i_{cam}(x, t) = \left\{ \begin{array}{l} |A(x)R_{diffuse}(x) \otimes h_{cam}(x)|^2 + \\ |A_{probe}(x)R_{diffuse}(x) \otimes h_{cam}(x)|^2 + \\ \exp(i\Delta vt) \times (A(x)R_{diffuse}(x) \otimes h_{cam}(x)) \times \\ \text{conj}(A(x)R_{diffuse}(x) \otimes h_{cam}(x)) + \\ \exp(-i\Delta vt) \times (A_{probe}(x)R_{diffuse}(x) \otimes h_{cam}(x)) \times \\ \text{conj}(A_{probe}(x)R_{diffuse}(x) \otimes h_{cam}(x)) \end{array} \right\} \quad (15)$$

The first term in equation (15) represents the zeroth-order field contribution. The second and third terms represent the hologram and twin contributions. It is shown from equation (15) that the temporal frequency associated with the hologram term is distinct from the other terms. As such, a synchronous demodulation strategy that exploits the orthogonality of complex sinusoids may be used in isolating the hologram term from the other terms. Synchronous demodulation may be implemented by the lock-in camera 460. In some implementations, a single-pixel detector, focal-plane array detector, or other similar devices may be used for synchronous demodulation to recover the hologram of the hidden object 440 from other corrupting fields.

Figure 5:
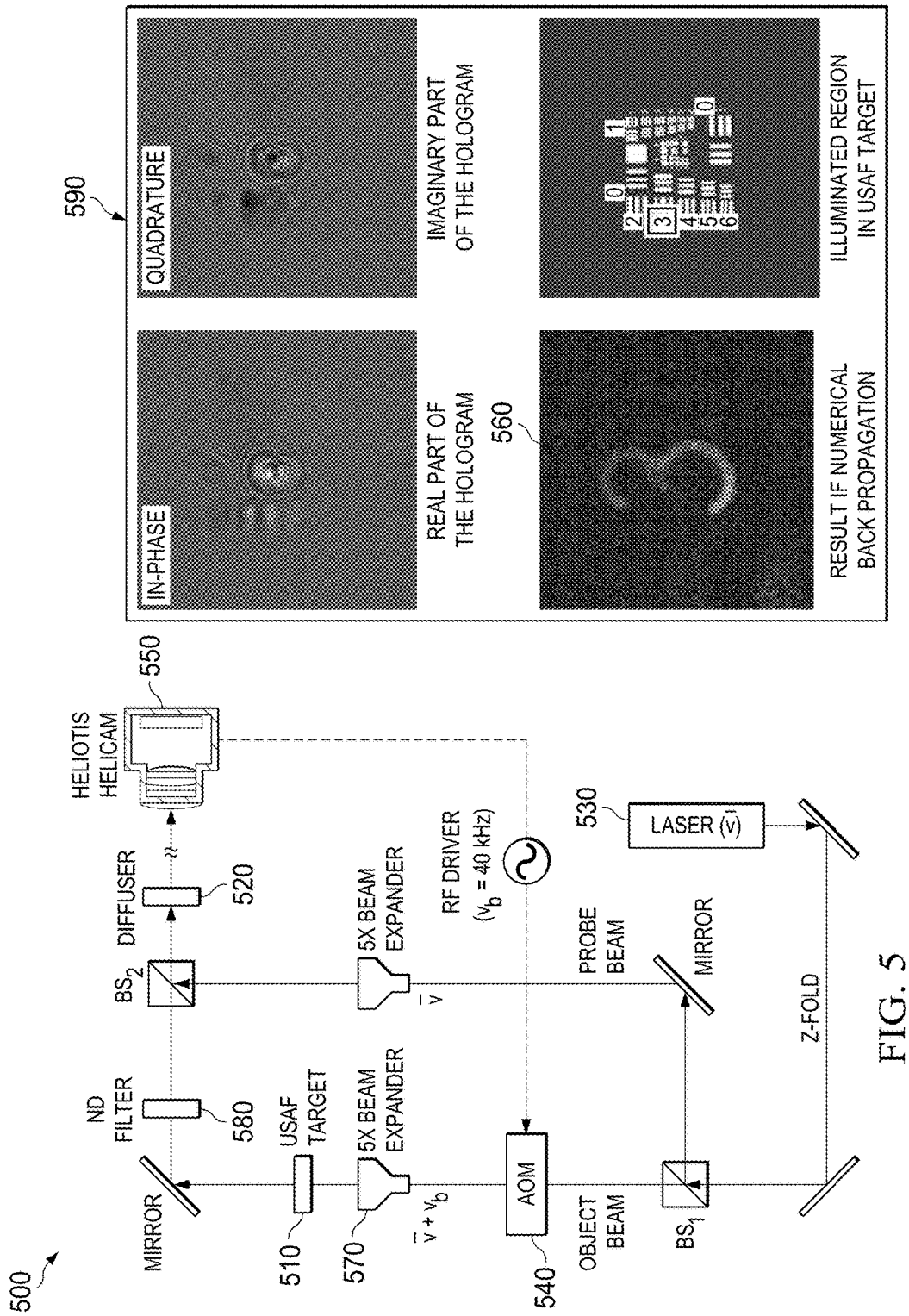
FIG. 5 illustrates an example experimental single-shot imaging system for recovering an image and the corresponding experiment result.

FIG. 5 illustrates an example experimental single-shot imaging system 500 for recovering an image and the corresponding experiment result 590. In this example, the experimental imaging system 500 may be used to recover the hologram of a transmissive resolution target 510 hidden behind a diffuser 520. The example imaging system 500 can be set up based on a Mach-Zehnder interferometer adapted for hologram recovery. In the particular experiment, light from a 532 nm linearly-polarized collimated laser source 530 (e.g., Vortran Stardus 532-40, beam diameter 0.8 mm) can be used to provide the illumination beam and probe beam for the interferometer. One or more AOMs 540 (e.g., Intraaction AOM-802AF1) may be used to upshift the temporal frequency of the illumination beam by 40 KHz, relative to the temporal frequency of the probe beam. The illumination beam modulated by the AOM 540 may be expanded using a 5× Beam expander 570. An example United States Air Force (USAF) resolution target (RES-1, Newport) inserted in the illumination path is used as the hidden target 510. A neutral density (ND) filter 580 can be adopted to introduce a power mismatch between the two beams, where the optical density of the ND 580 equals 1. Light from the two beams is combined using a non-polarizing beam splitter (BS$_2$) before being directed towards a diffuser 520 (e.g., Thorlabs DG100X100-1500) that obscures the view of the hidden target 510. A lock-in camera 550A (Heliotis Helicam C3) observing the light distribution at the diffuser 520 can provide a hologram of the hidden target 510. The real and imaginary components of the acquired hologram are shown in the image insets 590 of FIG. 5. It is shown in the result image 560 that the example imaging system 500 can fully resolve the number "3", following back-propagation from the diffuser 520 to the hidden target 510.

Figure 6A:
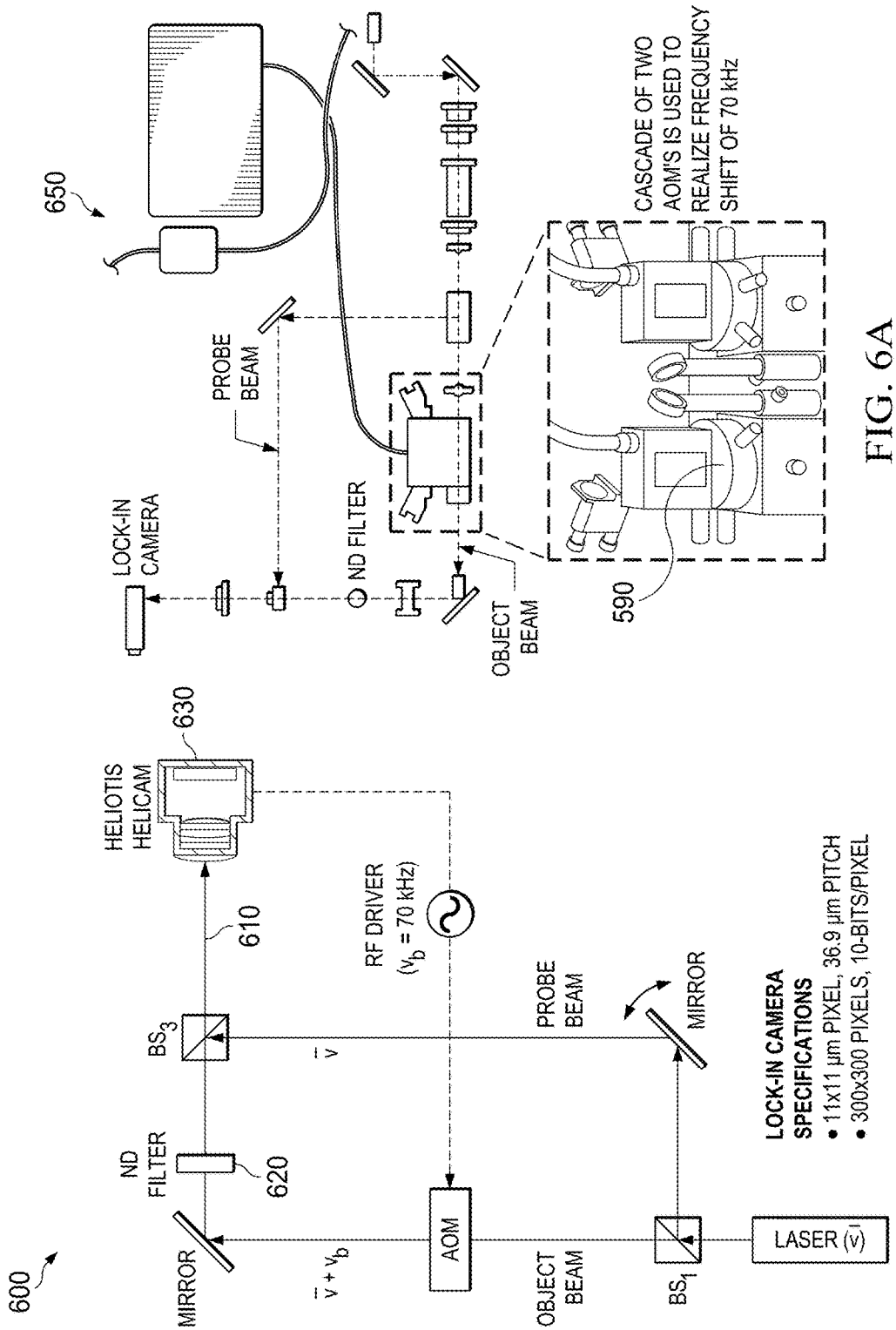
FIG. 6A illustrates another example experimental single-shot imaging system for recovering an image and the corresponding experiment apparatuses.

FIG. 6A illustrates another example experimental single-shot imaging system 600 for recovering an image and the corresponding experiment apparatuses 650. The example experiment 600 may be used to validate the single-shot hologram recovery concept. The example experimental apparatuses 650 may be set up as a Mach-Zehnder interferometer adapted for hologram recovery. In this experiment, the goal is to detect the hologram in the recombination arm 610 of the example imaging system 600. The example imaging system 600 may include interferometric apparatuses, a ND filter 620, and a lock-in camera 630. In some cases, the lock-in camera 630 can only discern a weak sinusoid against a strong background. In other words, the power of the hologram component can be much weaker than the zeroth-order and twin components, which makes it difficult to be isolated. The inclusion of the ND filter 620 may help examine the impact of power mismatch on the ability to recover the complex fields of the hologram. The results of the example experiment 600 are illustrated in FIG. 6B.

Figure 6B:
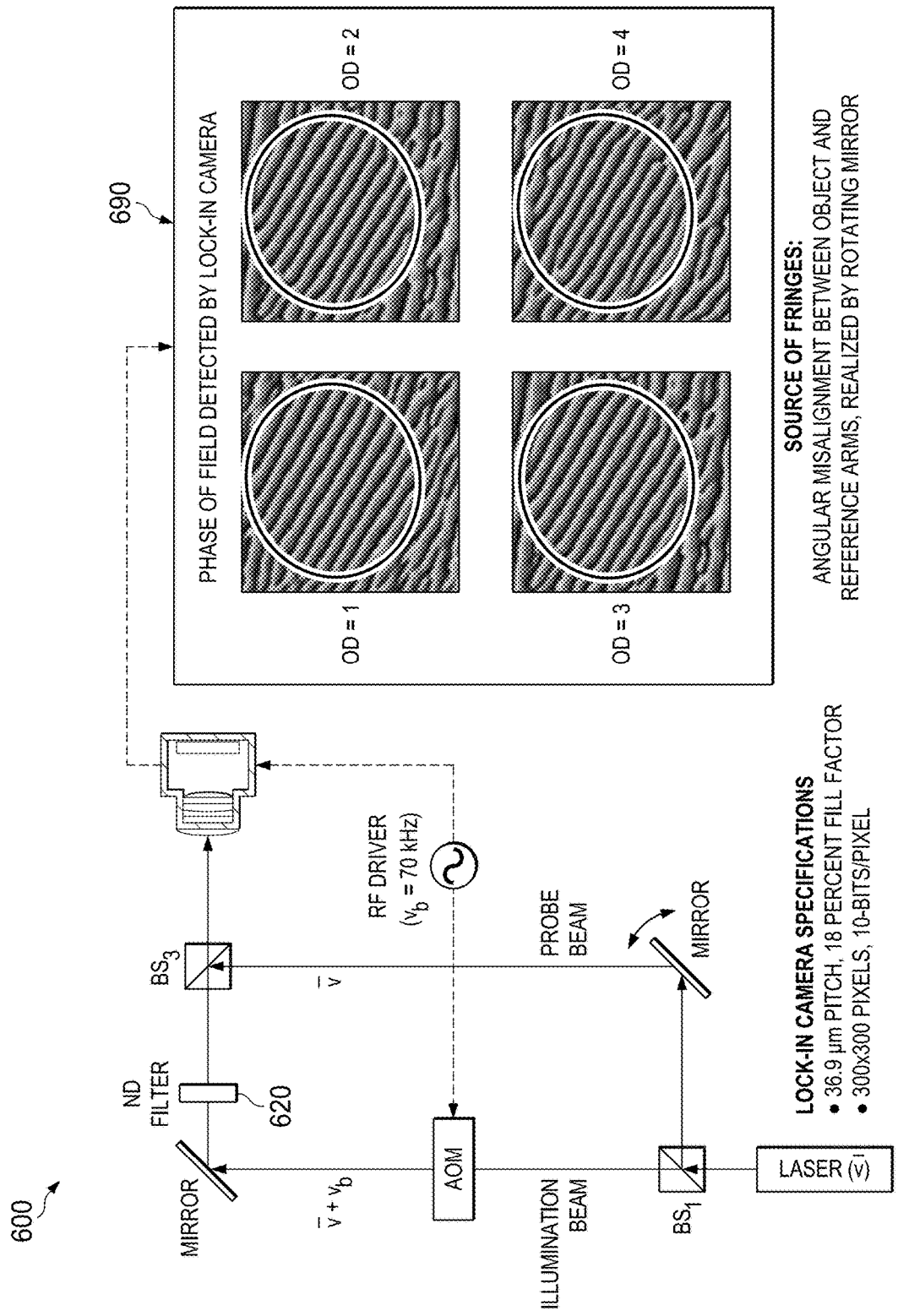
FIG. 6B illustrates experiment result of the example experimental single-shot imaging system.

FIG. 6B illustrates experiment result 690 of the example experimental single-shot imaging system 600. The fringes observed in the phase of the estimated hologram 690 arise from the deliberate angular misalignment of the illumination beam and the probe beam. As shown in the image insets 690 in FIG. 6B, the power mismatch does not have an adverse impact on the ability to recover complex-valued fields in a Mach-Zehnder heterodyne interferometer 600. The single-shot phase retrieval using the example experimental imaging system 600 also shows insensitivity to fringe drift arising from pointing errors in the illumination beam and/or the probe beam.

Figure 7:
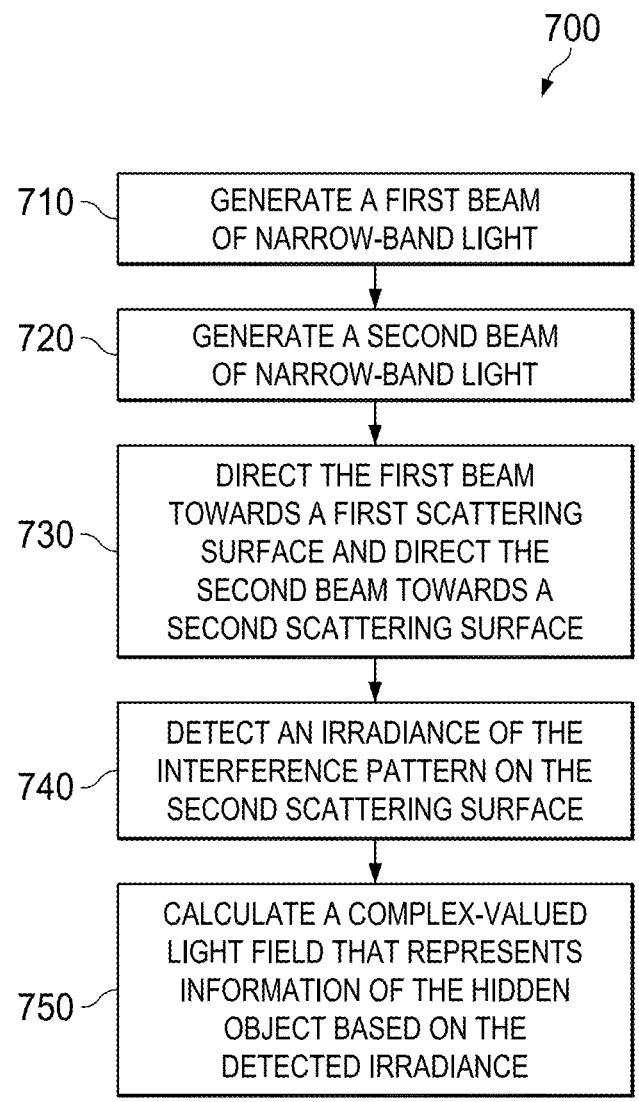
FIG. 7 is a flowchart illustrating an example process of recovering information of an object hidden from view.

FIG. 7 is a flowchart illustrating an example process 700 of recovering information of an object hidden from view. The example process 700 may be performed by any imaging system or imager in accordance with the disclosure.

At 710, a light source generates a first beam of narrow-band light.

At 720, the light source generates a second beam of narrow-band light. In some cases, the light source may be a laser source, one or more light emitting diodes, or a broadband light source with a narrow-band light filter. In some cases, the light source may include a narrow-band light source that can emit narrow-band light and a first beam splitter that can split the narrow-band light to the first beam and the second beam. In some cases, the narrow-band light may be a coherent light and a linewidth of the narrow-band light may be less than or equal to one nanometer. In some cases, the narrow-band light has a frequency range in a visible portion of an electromagnetic spectrum, an infrared, an ultraviolet, or a millimeter wave spectrum. In some cases, the first beam may be an illumination beam and second beam may be a probe beam.

At 730, the first beam is directed towards a first scattering surface and the second beam is directed towards a second scattering surface. Both the first scattering surface and the second scattering surface may have a surface roughness greater than a wavelength of light. The first scattering surface may scatter the first beam to a scattered light that illuminates a hidden object. The hidden object may reflect at least a portion of the scattered light towards the second scattering surface. The at least a portion of the scattered light may interfere with the second beam and produce an interference pattern on the second scattering surface.

In some cases, a phase modulator can modulate the phase of the second beam to introduce a first phase shift of the second beam and the first phase shifted second beam may interfere with the light field of the scattered first beam diffracted by the hidden object to create a second interference pattern on the second scattering surface. In such cases, the light distribution on the second scattering surface may include the first interference pattern and the second interference pattern.

In some cases, the phase modulator can modulate the phase of the second beam to introduce a second phase shift of the second beam and the second phase shifted second beam may interfere with the light field of the scattered first beam diffracted by the hidden object to create a third interference pattern on the second scattering surface. In such cases, the light distribution on the second scattering surface may include the first interference pattern, the second interference pattern, and the third interference pattern.

In some cases, the phase modulator can modulate the phase of the second beam to introduce a third phase shift of the second beam and the third phase shifted second beam may interfere with the light field of the scattered first beam diffracted by the hidden object to create a fourth interference pattern on the second scattering surface. In such cases, the light distribution on the second scattering surface may include the first interference pattern, the second interference pattern, the third interference pattern, and the fourth interference pattern. In some implementations, the phase modulator may instead modulate the phase of the first beam to produce the first, second, third, and/or fourth interference pattern.

At 740, an image sensor may be properly positioned to detect an irradiance of the interference pattern on the second scattering surface. A line-of-sight between the image sensor and the hidden object may be obstructed.

At 750, an image processor that calculates a complex-valued light field that represents information of the hidden object based on the detected irradiance of the interference pattern on the second scattering surface. The information of the hidden object may include a hologram, an image, or any geometry information of the hidden object. In some cases, the image processor may further perform numerical approximation to identify a hologram of the hidden object based on the complex-valued light field. In some cases, the image processor may perform numerical approximation to identify an image of the hidden object based on a magnitude component of the complex-valued light field. In some cases, the image processor may perform numerical approximation to identify a geometry of the hidden object based on a phase component of the complex-valued light field. In some implementations, the image processor may further perform a field propagation, a Fourier transform, or a numerical approximation of the complex-valued light field.

A number of embodiments of the invention have been described. Nevertheless, it will be understood that various modifications may be made without departing from the spirit and scope of the invention.

What is claimed is:

1. An imaging system for identifying information of an object hidden from view, the imaging system comprising:
    a light source that generates a first beam of narrow-band light and a second beam of narrow-band light that has temporal fluctuations correlated with the first beam;
    wherein the first beam is directed towards a first scattering surface and the second beam is directed towards a second scattering surface, both the first scattering surface and the second scattering surface having a surface roughness greater than a wavelength of light, and wherein the first scattering surface scatters the first beam to a scattered light that illuminates a hidden object, the hidden object reflects at least a portion of the scattered light towards the second scattering surface, the at least a portion of the scattered light interferes with the second beam and produces an interference pattern on the second scattering surface;
    a first phase modulator positioned along the propagation direction of the second beam that modulates a phase of the second beam to introduce a first phase shift of the second beam and the first phase shifted second beam interferes with the light of the first beam reflected by the hidden object to produce a second interference pattern on the second scattering surface;
    an image sensor positioned to detect irradiance of the interference pattern on the second scattering surface, wherein a line-of-sight between the image sensor and the hidden object is obstructed; and
    an image processor that calculates a complex-valued light field that represents information of the hidden object based on the detected irradiance of the interference pattern on the second scattering surface.

2. The imaging system of claim 1, wherein the first phase modulator modulates the phase of the second beam to introduce a second phase shift of the second beam and the second phase shifted second beam interferes with the light of the first beam reflected by the hidden object to produce a third interference pattern on the second scattering surface.

3. The imaging system of claim 2, wherein the first phase modulator modulates the phase of the second beam to introduce a third phase shift of the second beam and the third phase shifted second beam interferes with the light of the first beam reflected by the hidden object to produce a fourth interference pattern on the second scattering surface.

4. The imaging system of claim 1, wherein the first scattering surface at least partially overlaps with the second scattering surface.

5. The imaging system of claim 1, wherein the narrow-band light is coherent and a linewidth of the narrow-band light is less than or equal to one nanometer.

6. The imaging system of claim 1, wherein the light source is a laser source, one or more light emitting diodes, a narrow-band light filter, or a broadband light source with a narrow-band light filter.

7. The imaging system of claim 1, wherein the narrow-band light has a frequency range in a visible portion of an electromagnetic spectrum, an infrared, an ultraviolet, or a millimeter wave spectrum.

8. The imaging system of claim 1, wherein the complex-valued light field represents a hologram of the hidden object, and the image processor further performs numerical approximation to identify the hologram of the hidden object.

9. The imaging system of claim 1, wherein the image processor further performs numerical approximation to identify an image of the hidden object based on a magnitude component of the complex-valued light field.

10. The imaging system of claim 1, wherein the image processor further performs numerical approximation to identify a geometry of the hidden object based on a phase component of the complex-valued light field.

11. The imaging system of claim 1, wherein the image processor further performs a field propagation, a Fourier transform, or a numerical approximation of the complex-valued light field.

12. A method for identifying information of an object hidden from view, comprising:
    generating a first beam of narrow-band light to illuminate on a first scattering surface;
    generating a second beam of narrow-band light to illuminate on a second scattering surface, the second beam has temporal fluctuations correlated with the first beam, and the narrow-band light is coherent and a linewidth of the narrow-band light is less than or equal to one nanometer;
    wherein both the first scattering surface and the second scattering surface have a surface roughness greater than a wavelength of light, and wherein the first scattering surface scatters the first beam to a scattered light that illuminates a hidden object, the hidden object reflects at least a portion of the scattered light towards the second scattering surface, the at least a portion of the scattered light interferes with the second beam and produces an interference pattern on the second scattering surface;
    detecting, with an image sensor, irradiance of the interference pattern on the second scattering surface, wherein a line-of-sight between the image sensor and the hidden object is obstructed; and
    calculating a complex-valued light field that represents information of the hidden object based on the detected irradiance of the interference pattern on the second scattering surface.

13. The method of claim 12, further comprising:
    modulating a phase of the second beam to introduce a first phase shift of the second beam and the first phase shifted second beam interferes with the light of the first beam reflected by the hidden object to produce a second interference pattern on the second scattering surface;
    modulating the phase of the second beam to introduce a second phase shift of the second beam and the second phase shifted second beam interferes with the light of the first beam reflected by the hidden object to produce a third interference pattern on the second scattering surface; and
    modulating the phase of the second beam to introduce a third phase shift of the second beam and the third phase shifted second beam interferes with the light of the first beam reflected by the hidden object to produce a fourth interference pattern on the second scattering surface.

14. The method of claim 12, wherein the narrow-band light has a frequency range in a visible portion of an electromagnetic spectrum, an infrared, an ultraviolet, or a millimeter wave spectrum.

15. The method of claim 12, further comprises performing numerical approximation to identify a hologram of the hidden object based on the complex-valued light field.

16. The method of claim 12, further comprises performing numerical approximation to identify an image of the hidden object based on a magnitude component of the complex-valued light field.

17. The method of claim 12, further comprises performing numerical approximation to identify a geometry of the hidden object based on a phase component of the complex-valued light field.

18. The method of claim 12, further comprises performing a field propagation, a Fourier transform, or a numerical approximation of the complex-valued light field.

19. An imaging system for identifying information of an object hidden from view, the imaging system comprising:
- a light source that generates a first beam of narrow-band light and a second beam of narrow-band light that has temporal fluctuations correlated with the first beam, where the narrow-band light is coherent and a linewidth of the narrow-band light is less than or equal to one nanometer;
- wherein the first beam is directed towards a first scattering surface and the second beam is directed towards a second scattering surface, both the first scattering surface and the second scattering surface having a surface roughness greater than a wavelength of light, and wherein the first scattering surface scatters the first beam to a scattered light that illuminates a hidden object, the hidden object reflects at least a portion of the scattered light towards the second scattering surface, the at least a portion of the scattered light interferes with the second beam and produces an interference pattern on the second scattering surface;
- an image sensor positioned to detect irradiance of the interference pattern on the second scattering surface, wherein a line-of-sight between the image sensor and the hidden object is obstructed; and
- an image processor that calculates a complex-valued light field that represents information of the hidden object based on the detected irradiance of the interference pattern on the second scattering surface.

20. The imaging system of claim 19, wherein the first scattering surface at least partially overlaps with the second scattering surface.

\* \* \* \* \*